United States Patent [19]

Klemm

[11] Patent Number: Plant 7,410

[45] Date of Patent: Jan. 1, 1991

[54] GERANIUM NAMED KLECEROL

[75] Inventor: Siegfried Klemm, Stuttgart, Fed. Rep. of Germany

[73] Assignee: Klemm & Sohn, Stuttgart, Fed. Rep. of Germany

[21] Appl. No.: 356,195

[22] Filed: May 24, 1989

[51] Int. Cl.[5] ..... A01H 5/00
[52] U.S. Cl. ..... Plt./68
[58] Field of Search ..... Plt./68

[56] References Cited

U.S. PATENT DOCUMENTS

P.P. 5,373 12/1984 Schumann ..... Plt. 68
P.P. 6,717 4/1989 Duemmen ..... Plt. 68
P.P. 7,087 12/1989 Hofmann ..... Plt. 68

*Primary Examiner*—Howard J. Locker
*Attorney, Agent, or Firm*—Charles W. Rummler

[57] ABSTRACT

A new Geranium cultivar particularly distinguished by the large size of its flower clusters carried on strong, upright stems well above a compact foliage mass of medium green color, the foliage mass having a height of about 28 cm. and the flower stalks being of a length of about 18 to 20 cm. so that the flower clusters will stand at an average height of from 5 to 10 cm. above the foliage body. The florets are rather large having an average diameter of about 5.2 cm. and a definitely hot pink coloration and there is a sufficient number of florets in each cluster to make the cluster group provide a very brilliant coloration to enhance the entire floral display of this geranium plant.

1 Drawing Sheet

BACKGROUND OF THE NEW PLANT

This new Geranium cultivar originated as a seedling of a hybrid developed by me by crossing the geranium Blues (U.S. Plant Pat. No. 5,373) with an unknown pink variety selected from my collection of pelargonium varieties maintained at my nursery at Stuttgart, West Germany for breeding purposes. This particular seedling was selected by me from those produced by the said hybrid because of its very advantageous growth habit and its outstanding coloration. This particular seedling first bloomed in 1985 with such advantageous characteristics that I decided to propagate this seedling, which I did by means of cuttings at Stuttgart, West Germany, and the results were so satisfactory that under my direction this particular variety was propagated under controlled conditions, both indoors and outdoors, for almost four years which demonstrated conclusively that the advantageous characteristics of this variety would hold true from generation to generation and appeared to be firmly fixed. My new geranium cultivar is propagated vegetatively at my nursery at Stuttgart, West Germany for commercial purposes.

DESCRIPTION OF THE DRAWING

My new geranium cultivar illustrated by the accompanying photographic drawing which illustrates the form and floral display of the plant as well as the nature of its blooms and its bud clusters particularly with their relation to the background of the compacted foliage of a medium green color. The color designations specified herein are according to The R.H.S. Colour Chart published by the Royal Horticultural Society of London, England.

DESCRIPTION OF THE NEW PLANT

The following is a detailed description of my new variety of geranium plant based upon observations made at Stuttgart, West Germany, in 1988 of plants grown both indoors and outdoors under controlled conditions. The color designations stated herein being according to The R.H.S. Colour Chart of the Royal Horticultural Society of London, England.

THE PLANT

Origin: Seedling.
Seed parent: The variety named Blues (U.S. Plant Pat. No. 5,373).
Pollen parent: An unknown variety selected by me from my collection of geranium plants maintained at Stuttgart, West Germany.
Classification:
*Botanic.*—*Pelargonium zonale* Hybrid.
*Commercial.*—Geranium.
Form: A compact bush.
Height: About 28 cm., exclusive of the flower clusters.
Branching character: Very good.
Growth habit: Vigorous with good strength.
Foliage:
*Quantity.*—Normal.
*Leaf size.*—Medium, of reniform shape and with bicrenate margins.
*Texture.*—Smooth.
*Color.*—Upper side — Medium green with almost no zonation. Under side — Light green.

THE BUD

Size: Large.
*Diameter.*—About 11 mm.
*Length.*—About 14 mm.
Shape: Ovoid with pointed apex.
Rate of opening: Medium.
Color of floret petals:
*When sepals first divide.*—Light Pink.
*When petal begin to unfurl.*—Hot Pink.
Sepals:
*Number.*—Five.
*Shape.*—Elongate with acute apex.
*Character.*—The sepals stand up when the flower is open.
*Color.*—Green, both inside and outside.
Striae: None.

Calyx:
*Size.*—Broad.
*Shape.*—Cup-shaped.
*Splitting.*—The calyx does not split.
*Aspect.*—Slightly hairy.
Peduncle:
*Length.*—Averages about 15 cm.
*Character.*—Rigid and erect.
*Color.*—Green.

INFLORESCENCE

Blooming habit: Continuous and profusely from early Spring through Midseason into Fall.
Size of flower cluster: Medium with a diameter of 10 to 11 cm.
Florets:
*Size.*—Medium. Diameter — About 5.2 cm. Depth — 1 to 1.5 cm.
Borne: Singly on an umbel stem.
Shape:
*When bloom first opens.*—Cup-shaped.
*When bloom matures.*—The flower flattens.
Petalage:
*Number of petals.*—Seven to eight.
*Arrangement.*—Imbricated.
*Form.*—Broad with rounded apex and entire margins.
*Texture.*—Soft.
*Appearance.*—Satiny.
*Color.*—In general, Rose Begal, RHS 57-C with the main middle portion of the body being a Hot Pink, RHS 67-C. Center of the petal base — White.
Flower stem:
*Length.*—About 18 to 20 cm.
*Character.*—Upright with good strength.
*Color.*—Green.
Discoloration after full bloom: None.

Effect of wet or hot weather: None.
Persistence: The petals of mature florets dry and drop off.
Disease resistance: The plant and its blooms are resistant to botrytis as observed at Stuttgart, West Germany through 1985 and 1986.
Lasting quality of florets: About sixteen days.

THE REPRODUCTIVE ORGANS

Stamens:
*Number.*—Seven.
*Arrangement.*—Encircling the pistil.
*Anthers.*—Size: About 1.5 mm. Color: Dark orange.
*Filaments.*—Length: About 4 mm. Color: Light Pink.
*Pollen.*—Color: Orange.
Pistils:
*Number.*—One.
*Style.*—Length: About 4.5 mm. Color: Frosted Pink.
*Stigmas.*—Character: Five-Lobed.

THE FRUIT

Fertility: The fruit is fertile.
Shape: Ovoid.
Color at maturity: Dark brown.

This plant is a very new variety and differs from other of the same general character by its relatively large hot pink blooming clusters.

I claim:

1. The new and distinctive Geranium cultivar substantially as herein shown and described and distinguished by its relatively large flower clusters of a generally Hot Pink coloration, and the round compacted shape of the foliage base above which the flower clusters stand.

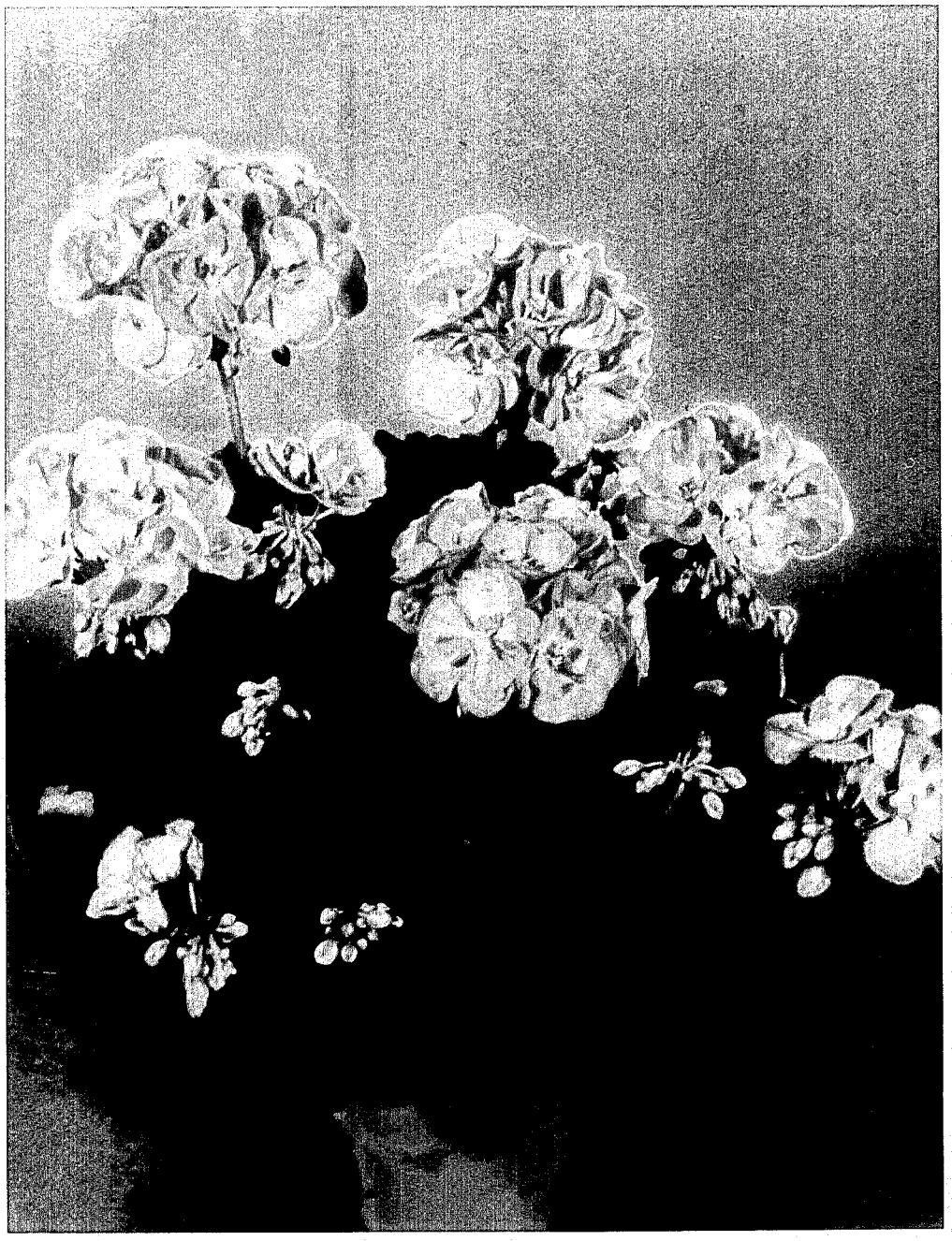

* * * * *